(12) United States Patent
Gibb et al.

(10) Patent No.: US 11,261,169 B2
(45) Date of Patent: Mar. 1, 2022

(54) MANUFACTURING METHOD FOR AND INSECTICIDAL COMPOSITIONS COMPRISING THIOCYCLAM HYDROCHLORIDE

(71) Applicant: Arysta Lifescience North America, LLC, Cary, NC (US)

(72) Inventors: Cameron S. Gibb, Apex, NC (US); Christopher L. Larson, Cary, NC (US); Mark T. Singleton, Morris, CT (US); Kamal L. Kataria, Maharashtra State (IN); Samantha Besse, Daban (FR); Joseph A. Moore, III, Wake Forest, NC (US); Thomas C. Lovelace, Apex, NC (US); Chandra S. Kanugala, Telangana (IN); Srinivas Vollala, Telangana (IN); Balraju Vadla, Telangana (IN)

(73) Assignee: ARYSTA LIFESCIENCE NORTH AMERICA, LLC, Cary, NC (US)

( * ) Notice: Subject to any disclaimer, the term of this patent is extended or adjusted under 35 U.S.C. 154(b) by 178 days.

(21) Appl. No.: 16/808,871

(22) Filed: Mar. 4, 2020

(65) Prior Publication Data
US 2020/0216408 A1 Jul. 9, 2020

Related U.S. Application Data

(62) Division of application No. 15/268,734, filed on Sep. 19, 2016, now abandoned.

(51) Int. Cl.
*C07D 341/00* (2006.01)
*A01N 43/32* (2006.01)
*A01N 43/80* (2006.01)

(52) U.S. Cl.
CPC .......... *C07D 341/00* (2013.01); *A01N 43/32* (2013.01); *A01N 43/80* (2013.01)

(58) Field of Classification Search
None
See application file for complete search history.

(56) References Cited

U.S. PATENT DOCUMENTS

| | | | |
|---|---|---|---|
| 3,917,814 A | 11/1975 | Hedges et al. | |
| 4,614,821 A | * 9/1986 | Kihara | C07D 339/04 544/145 |
| 6,048,892 A | 4/2000 | Iwasaki et al. | |
| 2002/0099174 A1 | 7/2002 | Johnston et al. | |
| 2003/0166618 A1 | 9/2003 | Senn et al. | |
| 2008/0293676 A1 | 11/2008 | Fischer et al. | |
| 2018/0079739 A1 | 3/2018 | Gibb et al. | |
| 2020/0216409 A1 | 7/2020 | Gibb et al. | |

FOREIGN PATENT DOCUMENTS

| | | |
|---|---|---|
| AU | 7002481 A | 11/1981 |
| CN | 1355167 A | 6/2002 |
| CN | 102388892 A | 3/2012 |
| CN | 103755680 A | 4/2014 |
| WO | 2008128690 A2 | 10/2008 |

OTHER PUBLICATIONS

European Search Report for Application 14851492.3 [PCT/US2017/051449] dated Apr. 15, 2020; 11 pages.
International Search Report and Written Opinion for International Application PCT/US2019/036851; International Filing Date: Jun. 12, 2019; dated Sep. 3, 2019; 6 pages.
International Search Report and Written Opinion for International Application PCT/US2017/051449; International Filing Date: Sep. 14, 2017; dated Jan. 11, 2018; 11 pages.
Allah, A. et al.; "A Trial for Rational Chemical Control of Red SPider Mite and Beanfly Attacking Three Varieties of the Bean Plants"; Egyptian Journal of Agricultural Research, vol. 88, Issue No. 1; 2010; pp. 49-67.
Aneni, T. et al.; "Efficacy of Stamina 50 (Thiocyclam hydrogenoxalate) on Coelaenomenodera elaeidis (Coleoptera—Chrysomelidae—Hispinae) in Okumu oil palm plantation, Nigeria"; Journal of Applied and Natural Science, vol. 4, Issue No. 1; 2012; pp. 30-35.

* cited by examiner

*Primary Examiner* — Jeffrey S Lundgren
*Assistant Examiner* — Michael J Schmitt
(74) *Attorney, Agent, or Firm* — Cantor Colburn LLP

(57) ABSTRACT

A method for manufacturing an insecticidal compound and insecticidal compositions comprising the insecticidal compound and methods of use are presented herein. The manufacturing method presented herein allows for a high purity grade of thiocyclam hydrochloride to be synthesized. The insecticidal compositions comprising the thiocyclam hydrochloride can be used for prevention of crop destruction by insects. The use of thiocyclam hydrochloride in insecticidal compositions as described herein can achieve greater efficacy than previously known insecticides, by eliminating the insect pests more reliably and efficiently.

10 Claims, 1 Drawing Sheet

Reaction Scheme

Formula (2)

MANUFACTURING METHOD FOR AND INSECTICIDAL COMPOSITIONS COMPRISING THIOCYCLAM HYDROCHLORIDE

CROSS-REFERENCE TO RELATED APPLICATIONS

This application is a divisional of U.S. application Ser. No. 15/268,734, filed on Sep. 19, 2016, which is incorporated herein by reference in its entirety.

FIELD OF THE INVENTION

Embodiments herein relate generally to the manufacturing and use of the compound thiocyclam hydrochloride and/or solvate thereof, to control insect pests on plants, plant parts and locus thereof, including agricultural crops.

BACKGROUND OF THE INVENTION

Insecticides are pesticides that are formulated to kill, harm, repel or mitigate one or more species of insect. Insecticides work in different ways. Some insecticides disrupt the nervous system, whereas others may damage their exoskeletons, repel them or control them by some other means. They can also be packaged in various forms including sprays, dusts, gels and baits. Because of these factors, each insecticide can pose a different level of risk to non-target insects, people, pets and the environment.

Insecticides are chemicals used to control insects by killing them or preventing them from engaging in behaviors deemed undesirable or destructive. They are classified based on their structure and mode of action. Many insecticides act upon the nervous system of the insect (e.g., Cholinesterase (ChE) inhibition) while others act as growth regulators or endotoxins.

Insecticides are commonly used in agricultural, public health, and industrial applications, as well as household and commercial uses (e.g., control of roaches and termites). The most commonly used insecticides are the organophosphates, pyrethroids and carbamates. The USDA has reported that insecticides accounted for 12% of total pesticides applied to the surveyed crops. Corn and cotton account for the largest shares of insecticide use in the United States.

Insecticides include substances such as ovicides and larvicides used against insect eggs and larvae, respectively. Insecticides are claimed to be a major factor behind the increase in agricultural 20th century's productivity. Nearly all insecticides have the potential to significantly alter ecosystems; many are toxic to humans and some concentrate along the food chain.

Insecticides can be classified in two major groups: systemic insecticides, which have residual or long-term activity; and contact insecticides, which have no residual activity.

Systemic insecticides become incorporated and distributed systemically throughout the whole plant. When insects feed on the plant, they ingest the insecticide. Systemic insecticides produced by transgenic plants are called plant-incorporated protectants. For instance, a gene that codes for a specific Bacillus thuringiensis biocidal protein was introduced into corn and other species. The plant manufactures the protein, which kills the insect when consumed. Systemic insecticides have activity pertaining to their residue which is called "residual activity" or long-term activity.

Contact insecticides are toxic to insects upon direct contact. These insecticides commonly fall into three categories. First, there are natural insecticides, such as nicotine, pyrethrum and neem extracts, made by plants as defenses against insects. Second there are inorganic insecticides, which are metals such as arsenates, copper and fluorine compounds. Third are organic insecticides, which are organic chemical compounds, typically working by direct contact with the insect or eggs and larvae.

Insecticides are applied in various formulations and delivery systems such as sprays, baits, and slow-release diffusion. Efficacy can be related to the quality of pesticide application, with small droplets, such as aerosols often improving performance.

Current treatments for controlling insects typically include chemicals, biologicals, and/or non-chemical methods such as systemic acquired resistance inducers to provide resistant crop strains, GMO's, and hatching stimulants and inhibitors to clear loci prior to planting. Each of these current treatments and methods has one or more drawbacks, including toxicity, cost, availability, reliability, and high application amounts. New insecticidal compositions also face elevated government regulations and public scrutiny as to their environmental and ecological impacts.

While it is difficult to isolate the effect of one pest in an ecological system, the estimated overall average yearly yield loss due to insects is estimated at around 10-15% worldwide, with a monetary value estimated in the billions of dollars. There are a wide variety of insects that insecticides target in the agricultural industry.

Insects (from Latin insectum, a calque of Greek ἔντομον [éntomon], "cut into sections") are a class of invertebrates within the arthropod phylum that have a chitinous exoskeleton, a three-part body (head, thorax and abdomen), three pairs of jointed legs, compound eyes and one pair of antennae. They are the most diverse group of animals on the planet, including more than a million described species and representing more than half of all known living organisms. The number of insect species is estimated to be between six and ten million, and potentially represent over 90% of the differing animal life forms on Earth. Insects may be found in nearly all environments.

In insects, there are nicotinic acetylcholine receptors (nAChR) in the parts of the postsynaptic membrane connecting nerves. Nereistoxin based compounds have long been known as agents that act on this location. Currently, common insecticides for preventing and killing target insects include compounds such as cartap hydrochloride, for use in agricultural crops.

Cartap, as shown in FIG. 1, is a pesticide that was first introduced into the market in Japan in 1967. Its commercial names include Padan, Kritap, AG-Tap, Thiobel, and Vegetox. The basic chemical structure is S, S-[2-(dimethylamino)-1, 3-propanediyl] dicarbamothioate. The residue left by this type of pesticide poses a threat to human health and therefore it would be desirable to find alternative compounds to those such as cartap, that can be applied at reduced concentrations with similar, or ideally, increased efficacy as an insecticide.

Embodiments herein provide manufacturing of an insecticidal compound and compositions and methods that can overcome reduced efficiency and high application concentrations of current insecticides.

SUMMARY OF THE INVENTION

It is an object of the current invention to provide a method of manufacturing a novel insecticide compound.

It is an object of the current invention to provide a method of manufacturing thiocyclam hydrochloride.

It is another object of the current invention to provide a method of manufacturing thiocyclam hydrochloride with 90% or higher purity.

It is yet another object of the current invention to provide a method of manufacturing thiocyclam hydrochloride with 95% or higher purity.

It is an object of the current invention to provide a method of manufacturing thiocyclam hydrochloride with greater than 30% yield.

It is an object of the current invention to provide a method of manufacturing thiocyclam hydrochloride with greater than 60% yield.

It is an object of the present invention to provide an insecticidal composition effective against insect pests.

It is another object of the present invention to provide an insecticidal composition that is effective against moths, soybean looper, aphids, and white flies.

It is still another object of the present invention to provide an improved insecticidal composition that is effective against insects and that can be readily applied to crops.

It is still another object of the present invention to provide an improved insecticidal composition that is effective on radish and bean crops.

It is still another object of the present invention to provide an insecticidal composition that is effective against insect pests that comprises thiocyclam hydrochloride and/or solvate thereof.

It is still another object of the present invention to develop a new class of insecticides with novel activity and which are highly effective when applied directly to crops and used in chemirrigation processes.

It is yet another object of the present invention to provide an improved insecticide composition with high efficacy at a low dose of thiocyclam hydrochloride and/or solvate thereof.

To that end, in one embodiment, the present invention relates generally to a method of manufacturing-N,N-dimethyl-1,2,3-trithian-5-ylamine hydrochloride comprising the steps of:
a) providing a mixture of thiosulfuric acid S,S'[2-(dimethylamino)trimethylene] ester monosodium salt and sodium hydroxide;
b) adding an aqueous saline solution to the mixture of thiosulfuric acid S,S'-[2-(dimethylamino)trimethylene] ester monosodium salt and sodium hydroxide, wherein the aqueous saline solution is added over the course of at least 3 hours;
c) separating the phases of the mixture;
d) collecting the solids from the mixture using filtration;
e) washing the solids with organic solvent; and
f) drying the solids,
wherein the dried solids are N,N-dimethyl-1,2,3-trithian-5-ylamine hydrochloride.

In another preferred embodiment, the present invention relates generally to an insecticidal composition wherein the composition comprises:
a) N,N-dimethyl-1,2,3-trithian-5-ylamine hydrochloride and/or a solvate thereof;
b) one or more auxiliary component; and
c) optionally, a safener.

In yet another preferred embodiment, the present invention relates generally to a method for prevention of insects on a crop using an insecticidal composition comprising:
a) N,N-dimethyl-1,2,3-trithian-5-ylamine hydrochloride and/or a solvate thereof;
b) one or more auxiliary compounds; and
c) optionally, a safener; and
wherein an insecticidally effective amount of the insecticidal composition is applied to a crop.

DETAILED DESCRIPTION OF THE PREFERRED EMBODIMENTS

Below is a detailed description of various exemplary embodiments. It shall be understood that the embodiments described herein are only used for illustrating and explaining, rather than being limiting. Included herein are novel manufacturing methods for the active ingredient in the inventive insecticidal compositions and methods for using such compositions.

Figure 1:
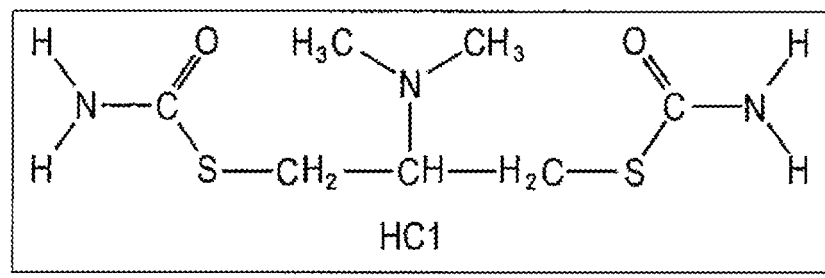
FIG. 1 provides the structure of cartrap.
Figure 2:
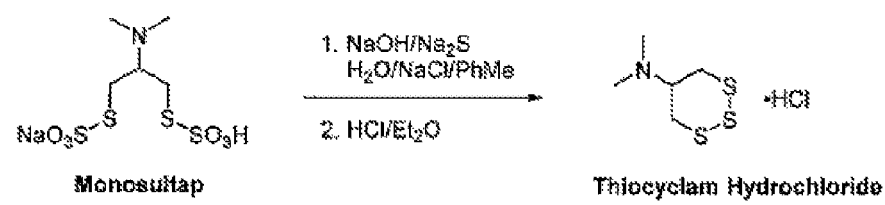
FIG. 2 provides a reaction scheme for thiocyclam hydrochloride.

The method of manufacturing thiocyclam hydrochloride is described in the reaction scheme of FIG. 2 and in the following examples. The inventors were surprisingly able to achieve acceptable yields and high purity of the insecticidal compound. High purity could not previously be achieved in production methods of thiocyclam hydrochloride and therefore its use in insecticidal compositions has not been found effective compared to other known insecticidal compounds. This is the first known effective synthetic method for thiocyclam hydrochloride.

Example 1

An aqueous saline solution of $Na_2S.9H_2O$ (17.1 g) was added to a stirring mixture of Monosultap (25 g), sodium hydroxide (2.86 g) and toluene/saline over 4.5 hours maintaining the temperature at −16 to −18° C. The reaction mixture was stirred at −16 to −18° C. until complete then filtered to remove inorganic salts. The cake was washed with toluene and combined with the filtrates. The phases were separated and the toluene solution was washed with water, then brine, and dried over sodium sulfate. 2M ethereal hydrochloric acid (50 mL) was added and the mixture was stirred for 1 hour. The solids formed were collected by filtration, washed with MTBE and dried to give thiocyclam hydrochloride in 87% yield (14.2 g) and 97.9% purity with 0.36% residual toluene.

Example 2

An aqueous saline solution of $Na_2S.9H_2O$ (15.3 g) was added to a stirring mixture of Monosultap (25 g), sodium hydroxide (3.16 g) and toluene/saline over 4 hours maintaining the temperature at −15 to −18° C. The reaction mixture was stirred at −15° C. until complete then filtered to remove inorganic salts. The cake was washed with toluene and the wash was combined with the filtrates. The phases were separated and the toluene solution was washed with water, then brine, and dried over sodium sulfate. 2M ethereal hydrochloric acid (50 mL) was added and the mixture was stirred for 1 hour. The solids formed were collected by filtration, washed with ice-cold MTBE and dried to give thiocyclam hydrochloride in 76% yield (12.4 g) and 98.3% purity bearing 0.22% residual toluene.

Example 3

An aqueous saline solution of $Na_2S.9H_2O$ (92.6 g) was added to a stirring mixture of Monosultap (100 g), sodium hydroxide (11.3 g) and toluene/saline/isopropanol over 5.5 hours maintaining the temperature at −20° C. The reaction mixture was stirred at −20° C. until complete then the phases were separated. The toluene solution was washed with water, then brine, and dried over sodium sulfate. 2M hydrochloric acid in isopropanol (224 mL) was added to the batch over 30 minutes and the mixture was stirred for 1 hour. The solids formed were collected by filtration, washed with isopropanol and dried to give thiocyclam hydrochloride in 60% yield (37.0 g) and 95.6% purity.

Example 4

A mixture of Monosultap (450 g), sodium hydroxide (51.3 g) and saline was added to a reactor containing toluene at −15 to −20° C. An aqueous saline solution of $Na_2S.9H_2O$ (308 g) was added to the hatch over 4 hours maintaining the temperature at −15° C. The reaction mixture was stirred at −15° C. until complete then the phases were separated. After an aqueous work-up, the organics were dried over magnesium sulfate and 2M ethereal hydrochloric acid (710 mL) was added. The mixture was stirred for 1 hour then the solids formed were collected by filtration. The cake was washed with toluene and dried to give thiocyclam hydrochloride in 68% yield (214 g) and 94.2% purity containing 0.55% residual toluene.

Example 5

An aqueous saline solution of $Na_2S.9H_2O$ (239.5 g) was added to a stirring mixture of Monosultap (350 g), sodium hydroxide (39.9 g) and toluene/saline over 3.5 hours maintaining the temperature at −16 to −18° C. The reaction mixture was stirred at −16 to −18° C. until complete then filtered to remove inorganic salts. The cake was washed with toluene and the wash was combined, with the filtrates. The phases were separated and the toluene solution was washed with water, then brine, and dried over sodium sulfate. 2M ethereal hydrochloric acid (680 mL) was added to the batch over 30 minutes and the mixture was stirred for 1 hour. The solids formed were collected by filtration, washed with ice-cold MTBE and dried to give thiocyclam hydrochloride in 33% yield (76.1 g) and 95.2% purity with 0.05% residual toluene.

The starting material in this novel reaction is Monosultap, which is a trade name for thiosulfuric acid S,S"-[2-(dimethylamino)trimethylene] ester monosodium salt; available from Sigma Aldrich. The CAS no. for Monosultap is 29547-00-0, the empirical formula is $C_5H_{12}NNaO_6S_4$ and its molecular weight is 333.40.

Figure 3:
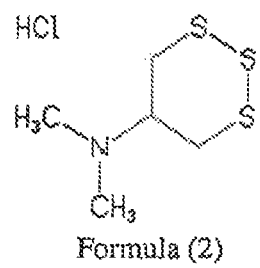
FIG. 3 provides the structure of Formula 2.

Thiocyclam hydrochloride is the common name for the compound of N,N-dimethyl-1,2,3-trithian-5-ylamine hydrochloride, with a molecular formula of $C_5H_{12}ClNS_3$, a relative molecular weight of 217.803, and with a structure of Formula (2) as shown in FIG. 3.

In some embodiments, there are provided insecticidal compositions comprising thiocyclam hydrochloride, as synthesized by the current inventors, wherein the lethal dose and lethal concentration of active insecticide is much lower than previously studied insecticides, therefore making thiocyclam hydrochloride an effective insecticide. These compositions are particularly useful in the elimination of target insects on agricultural crops.

Target sucking insects may include mosquitoes (for example *Aedes aegypti, Aedes vexans, Culex quinquefasciatus, Culex tarsalis, Anopheles albimanus, Anopheles stephensi, Mansonia titillans*), moth gnats (for example *Phlebotomus papatasii*), gnats (for example *Culicoides furens*), buffalo gnats (for example *Simulium damnosum*), stinging flies (for example *Stomoxys calcitrans*), tsetse flies (for example *Glossina morsitans morsitans*), horse flies (for example *Tabanus nigrovittatus, Haematopota pluvialis, Chrysops caecutiens*), true flies (for example *Musca domestica, Musca autumnalis, Musca vetustissima, Fannia canicularis*), flesh flies (for example *Sarcophaga carnaria*); myiasis-causing flies (for example *Lucilia cuprina, Chrysomyia chloropyga, Hypoderma bovis, Hypoderma lineatum, Dermatobia hominis, Oestrus ovis, Gasterophilus intestinalis, Cochliomyia hominivorax*), bugs (for example *Cimex lectularius, Rhodnius prolixus, Triatoma infestans*); lice (for example *Pediculus humanis, Haematopinus suis, Damalina ovis*), fleas (for example *Pulex irritans, Xenopsylla cheopis, Ctenocephalides canis, Ctenocephalides felis*), and sand fleas (*Tunga penetrans*). The current composition is especially effective for eliminating aphids and white flies.

Additional target species are Lepidoptera (moths and butterflies), which is the second largest order in the class Insecta. Nearly all lepidopteran larvae are called caterpillars. They have a well-developed head with chewing mouth parts. In addition to three pairs of legs on the thorax, they have two to eight pairs of fleshy abdominal prologs that are structurally different from the thoracic legs. Most lepidopteran larvae are herbivores; some species eat foliage, some burrow into stems or roots, and some are leaf-miners.

The composition and method of the present invention were found to be particularly advantageous for use in the control of insects in crops. Suitable target crops include, for example, cereals, including wheat, barley, rye, oats, rice, maize, sorghum, millet and manioc; beets, including sugar beets and fodder beets; fruits, including ponies, stone fruit and soft fruit, such as apples, pears, plums, peaches, almonds, cherries, or berries, for example strawberries, raspberries and blackberries; leguminous plants, including beans, lentils, peas and soybeans; oil plants, including rape, mustard, poppy, olives, sunflowers, coconut, castor oil plants, cocoa beans and groundnuts; cucurbitaceae, including marrows, cucumbers and melons; fibrous plants, including cotton, flax, hemp and jute; citrus fruit, including oranges, lemons, grapefruit and mandarins; vegetables, including spinach, lettuce, asparagus, cabbages, carrots, onions, tomatoes, potatoes and paprika; lauraceae, including avocados, cinnamon and camphor; as well as tobacco, nuts, coffee, aubergines, sugar cane, tea, pepper, vines, hops, bananas, natural rubber plants, eucalyptus, and ornamental plants. Examples of some preferred crops for insecticidal treatment include radish and beans.

As used herein, the term "insecticide" refers to a compound used to control (including prevention, reduction or elimination) parasitic insects. "Controlling insects" as used in the present invention means killing insects or preventing insects from developing or growing. Controlling insects as used herein also encompasses controlling insect progeny (development of viable cysts and/or egg masses). The compound described herein, may be used to keep an agricultural crop healthy and may be used curatively, preventively or systematically to control insects.

"Agricultural crops" as described herein, may refer to a wide variety of agricultural plants. When using the compounds described herein to keep a plant healthy, the controlling of insects includes the reduction of damage to plants and increased yield of the crop. The current invention achieves this endeavor by efficiently ridding a plant of insect pests by using a low concentration of the insecticidal composition to rid the crop of larger populations of insects than previous insecticides could eliminate.

Insecticidal effects typically relate to diminishing the occurrence or activity of the target insect. Such effects on the insect include necrosis, death, retarded growth, diminished mobility, lessened ability to remain on the host plant, reduced feeding and inhibition of reproduction. These effects on insects provide control (including prevention, reduction or elimination) of parasitic infestation of the plant. Therefore, the term "control" of a parasitic insect means achieving a pesticidal effect on the insect. The expressions "insecticidally effective amount" and "biologically effective amount" in the context of applying a chemical compound to control a parasitic insect refer an amount of the compound that is sufficient to protect an agricultural crop from destruction by such insects.

In the embodiments herein, the total content of components in the insecticidal composition is 100 weight percent.

The insecticidal compositions of the present invention may further contain one or more agriculturally acceptable auxiliaries. The auxiliaries employed in the insecticidal composition and their amounts will depend in part upon the type of formulation or composition and/or the manner in which the formulation is to be applied. Suitable auxiliaries include, but are not limited to formulation adjuvant or components, such as solvents, surfactants, stabilizers, antifoaming agents, anti-freezing agents, defoamers, emulsifiers, preservatives, antioxidants, colorants, thickeners and inert fillers and these auxiliaries may be used individually in the agrochemical composition or as a combination of one or e auxiliaries. Auxiliaries may be present in the composition anywhere from 0.01-90 parts by weight.

For example, the composition may comprise one or more solvents, which may be organic or inorganic. Suitable solvents are those that thoroughly dissolve the agrochemically active substance employed. Examples of suitable solvents include water, aromatic solvents, such as xylene (for example solvent products commercially available from Solvesso™), mineral oils, animal oils, vegetable oils, alcohols, for example methanol, butanol, pentanol, and benzyl alcohol ketones, for example cyclohexanone, and gamma-butyrolactone, pyrrolidones, such as NMP, and NOP, acetates; such as glycol diacetate, glycols, fatty acid dimethylamides fatty acids, and fatty acid esters.

The composition may optionally include one or more surfactants. Suitable surfactants are generally known in the art and include, but are not limited to, alkali metal, alkaline earth metal and ammonium salts of lignosulfonic acid, naphthalenesulfonic acid, phenol sulfonic acid, dibutyinaphthalenesulfonic acid, alkylarylsulfonates, alkylsulfates, alkylsulfonates, arylsulfonates, fatty alcohol sulfates, fatty acids and sulfated fatty alcohol glycol ethers, furthermore condensates of sulfonated naphthalene and naphthalene derivatives with formaldehyde, condensates of naphthalene or of naphthalenesulfonic acid with phenol, octylphenol, nonylphenol, alkylphenyl polyglycol ethers, tributylphenyl polyglycol ether, tristearylphenyl polyglycol ether, alkylaryl polyether alcohols, alcohol and fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite wake liquors and methylcellulose and ethylene oxide/propylene oxide block copolymers.

The composition may optionally comprise one or more polymeric stabilizers. Suitable polymeric stabilizers that may be used in the present invention include, but are not limited to, polypropylene, polyisobutylene, polyisoprene, copolymers of monoolefins and diolefins, polyacrylates, polystyrene, polyvinyl acetate, polyurethanes or polyamides.

The composition may include an anti-foaming agent. Suitable anti-foam agents include, for example, mixtures of polydimethylsiloxanes and perfluroalkylphosphonic acids, such as silicone anti-foam agents.

One or more preservatives may also be present in the composition. Suitable examples include, for example, Preventol® (commercially available from Bayer AG) and Proxel® (commercially available from Bayer AG).

Furthermore, the composition may also include one or more antioxidants, such as butylated hydroxytoluene.

The compositions may further comprise one or more solid adherents. Such adherents are known in the art and available commercially. They include organic adhesives, including tackifiers, such as celluloses of substituted celluloses, natural and synthetic polymers in the form of powders, granules, or lattices, and inorganic adhesives such as gypsum, silica, or cement.

The compositions may include one or more inert fillers, including, for example, natural ground minerals, such as kaolins, aluminas, talc, chalk, quartz, attapulgite, montmorillonite, and diatomaceous earth, or synthetic ground minerals, such as highly dispersed silicic acid, aluminum oxide, silicates, and calcium phosphates and calcium hydrogen phosphates. Suitable inert fillers for granules include, for example, crushed and fractionated natural minerals, such as calcite, marble, pumice, sepiolite, and dolomite, or synthetic granules of inorganic and organic ground materials, as well as granules of organic material, such as sawdust, coconut husks, corn cobs, and tobacco stalks.

The compositions may also include one or more thickeners, including, for example, gums, such as xanthan gum, PVOH, cellulose and its derivatives, clay hydrated silicates, magnesium aluminum silicates or a mixture thereof.

The insecticidal composition further may include a safener. The safener, also called antidote, may comprise, at least one of isoxadifen-ethyl, 1,8-dicarboxylic anhydride, mefenpyr-diethyl, fenchlorazole-ethyl, and cloquintocet-mexyl, and in some embodiments, isoxadifen-ethyl.

The dosage of the safener may be a conventional dosage used for matching the thiocyclam hydrochloride. In some embodiments, relative to 1 part by weight of thiocyclam hydrochloride, the safener has a content of from 0.1 to 10 parts by weight, or in some embodiments, from 0.5 to 5 parts by weight.

In some embodiments of the present invention, the insecticidal composition may be applied and used in pure form, or more preferably together with at least one of the auxiliaries, as described above.

The composition of the present invention may also comprise other active ingredients for achieving specific effects, for example, bactericides, fungicides, nematicides, molluscicides or herbicides. Suitable compounds are known in the art.

The insecticidal composition of the present invention may be formulated in different ways, depending upon the circumstances of its use. Suitable formulation techniques are known in the art and include water-dispersible powders, dusts, pastes, water-dispersible granules, solutions, emulsifiable concentrates, emulsions, suspension concentrates, aerosols, or microencapsulation suspensions.

Examples of formulation types for use in the present invention include the following:
 a) Water-soluble concentrates, in which thiocyclam hydrochloride and/or solvate thereof is dissolved in a water-soluble solvent. One or more wetting agents and/or other auxiliaries may be included. The active compound dissolves upon dilution with water.
 b) Emulsifiable concentrates, in which thiocyclam hydrochloride and/or solvate thereof is dissolved in a water-immiscible solvent, preferably with the addition of one or more non-anionic emulsifiers and anionic emulsifiers. The mixture is agitated, for example by stirring, to get a uniform formulation. Dilution with water provides a stable emulsion.
 c) Emulsions, in which thiocyclam hydrochloride and/or solvate thereof is dissolved in one or more suitable water-immiscible solvents, preferably with the addition of one or more non-anionic emulsifiers and anionic emulsifiers. The resulting mixture is introduced into water by appropriate means, such as an emulsifying machine, to provide a homogeneous emulsion. Dilution with water gives a stable emulsion.
 d) Suspensions, in which thiocyclam hydrochloride and/or solvate thereof is comminuted in an agitated ball mill, preferably with the addition of one or more dispersants and wetting agents, and water or solvent to give a fine active compound suspension. Dilution with water gives a stable suspension of the active compound.
 e) Water-dispersible granules and/or water-soluble granules in which thiocyclam hydrochloride and/or solvate thereof is ground finely, preferably with the addition of one or more dispersants and wetting agents, and prepared as water-dispersible or water-soluble granules by means of suitable techniques, for example by extrusion, drying in a spray tower, or by processing in a fluidized bed. Dilution with water gives a stable dispersion or solution of the active compound.

f) Water-dispersible powders and water-soluble powders, in which thiocyclam hydrochloride and/or solvate thereof is ground in a suitable apparatus, such as a rotor-stator mill, preferably with addition of one or more dispersants, wetting agents and silica gel. Dilution with water gives a stable dispersion or solution of the active compound.

g) Granules, in which thiocyclam hydrochloride and/or solvate thereof is finely ground in a suitable apparatus, with addition of up to 99.5 parts by weight of carriers. Granules can then be prepared either by suitable techniques, such as extrusion, spray-drying or using a fluidized bed.

In general, the composition or formulation is prepared and applied such that the insecticidal composition comprising thiocyclam hydrochloride and/or solvate thereof is applied at any suitable rate, as demanded by the insect to be treated. The application rate may vary within wide ranges and depends upon such factors as the type of application (i.e., foliar application, seed dressing, application in the seed furrow, etc.), the target crop plant, the particular insect(s) to be controlled, the climatic circumstances prevailing in each case, as well as other factors determined by the type of application, timing of application and target crop. Typically, the application rate may be from about 1 to about 2000 g of the insecticidal composition per hectare, and depending on the various factors described above, may be 10 to 1000 g/ha, more preferably 10 to 500 g/ha, more preferably 10 to 200 g/ha.

According to the present invention, the use of the insecticidal composition or formulation comprising thiocyclam hydrochloride and/or solvate thereof may be applied at any suitable time. In some embodiments, the composition is applied the locus of the plant prior to planting, during planting, or after planting. Such a treatment may take place by conventional methods known in the art, including, for example, drip-irrigation, chem-irrigation, and spray. In one embodiment, the insecticidal composition is contacted with the plant, plant part, or a locus thereof immediately before or immediately after the plant is transplanted.

For application to plant foliage, the insecticidal composition can be diluted up to about 600-fold or more with water, more typically up to about 100-fold or up to about 40-fold. Illustratively, a concentrate product can be applied at about 0.1 to about 30 liter/hectare (l/ha), for example about 5 to about 25 l/ha, in a total application volume after dilution of about 60 to about 600 l/ha, for example about 80 to about 400 l/ha or about 100 to about 200 l/ha. Other concentrations of the concentrate compositions disclosed herein can be used. One skilled in the art will recognize that a particular system may dictate a good working application rate which may depend in part on both the insects to be controlled as well as the crop requiring protection. The dosage range for the components of the inventive insecticidal composition allows for use of a reduced amount of active ingredient when used in the composition as described. The result is an inferior dosage rate that provides a more efficient insecticide.

As used herein, the term "about" refers to a measurable value such as a parameter, an amount, a temporal duration, and the like and is meant to include variations of +/−15% or less, preferably variations of +/−10% or less, more preferably variations of +/−5% or less, even more preferably variations of +/−1% or less, and still more preferably variations of +1-0.1% or less of and from the particularly recited value, in so far as such variations are appropriate to perform in the invention described herein. Furthermore, it is also to be understood that the value to which the modifier "about" refers is itself specifically disclosed herein.

According to the present invention, the use of the insecticidal composition comprising thiocyclam hydrochloride and/or solvate thereof for treating plants, plant parts, or a locus thereof is through the use of various processing methods carried out directly on the plant or plant parts or to the environment, the habitat or storage space of the plant or plant parts. These methods include, for example, dipping, spraying, atomizing, irrigation, evaporation, powdering, misting, fogging, spreading, foam, coating, painting, spreading-on, watering, soaking, drip irrigation, and chem-irrigation.

While certain forms of thiocyclam are known for use as a pesticide, the use of thiocyclam hydrochloride has not previously been successfully manufactured and therefore not contemplated for use as an insecticide. The reduced concentration and increased efficiency provided by the use of the synthesized thiocyclam hydrochloride were both surprising and unexpected. The following are non-limiting examples, wherein thiocyclam hydrochloride is compared to previously known insecticides, cartap and thiocyclam oxalate.

These examples are merely illustrations and are not to be understood as limiting the scope and underlying principles of the invention in any way. Various modifications of the invention in addition to those shown and described herein will become apparent to those skilled in the art form after the following examples and foregoing description. Such modifications are also intended to fall within the scope of the appended claims.

Example 1

Codling moth, Cydiapomonella—neonate larvae
Bioassay by diet incorporation
Mortality assessment 2 days after treatment
a.i. refers to active ingredient

| D + 2 | Purity of a.i. | LC50 (µg of a.i./ml of diet) | min | max | LC90 (µg of a.i./ml of diet) | min | max |
| --- | --- | --- | --- | --- | --- | --- | --- |
| Cartap | 50% | 10.14 | 7.98 | 12.87 | 104.80 | 74.72 | 157.80 |
| Thiocyclam oxalate | 87.5% | 3.57 | 3.00 | 4.25 | 19.76 | 15.53 | 26.32 |
| Thiocyclam HCl | 100% | 2.57 | 2.14 | 3.09 | 10.80 | 8.41 | 14.79 |

Example 2

Soybean looper, Chrysodeixis includens—3rd larval stage
Bioassay by diet surface incorporation
Mortality assessment 3 days after treatment
a.i. refers to active ingredient

| D + 3 | Purity of a.i. | LC50 (μg of a.i./ ml of diet) | min | max | LC90 (μg of a.i./ ml of diet) | min | max |
|---|---|---|---|---|---|---|---|
| Cartap | 50% | 53,069 | 31,907 | 106,810 | 908,897 | 346,473 | $4.64 \times 10^6$ |
| Thiocyclam oxalate | 87.5% | 173,363 | 52,529 | $2.38 \times 10^6$ | $8.55 \times 10^6$ | 906,914 | $1.53 \times 10^9$ |
| Thiocyclam HCl | 100% | 8,992 | 6,520 | 12,564 | 251,759 | 145,956 | 504,401 |

Example 3

Aphids *Myzus persicae*—larvae
Study based on IRAC n°019 methods, application method adapted
Plant: radish
Application on petri dish with larvae with a boom sprayer apparatus
Assessment of mortality 3 and 4 days after application
a.i. refers to active ingredient

|  | Purity of a.i. | LD50 (g a.i./ha) | min | max | LD90 (g a.i./ha) |
|---|---|---|---|---|---|
| D +3 | | | | | |
| Cartap | 50% | <18.18 | NA | NA | 36.70 |
| Thiocyclam oxalate | 87.5% | 7.99 | 1.40 | 54.98 | 38.06 |
| Thiocyclam HCl | 100% | 12.04 | 0.40 | 358.91 | 30.51 |
| D +4 | | | | | |
| Cartap | 50% | <18.18 | NA | NA | 16 |
| Thiocyclam oxalate | 87.5% | 5.35 | 2.60 | 10.27 | 29.57 |
| Thiocyclam HCl | 100% | 7.66 | 2.30 | 25.48 | 27.07 |

Example 4

Whiteflies, *Trialeurodes vaporarium*—larvae
Study based on IRAC n°015 methods, stage and application method adapted
Plant: bean
Application: On the petri dish with larvae with a boom sprayer apparatus
Assessment of mortality at 7, 9 and 14 days after application
a.i. refers to active ingredient

|  | Purity of a.i. | LD50 (g a.i./ha) | min | max | LD90 (g a.i./ha) |
|---|---|---|---|---|---|
| D +7 | | | | | |
| Cartap | 50% | 213.7 | 0.76 | $2.23 \times 10^8$ | $2.3 \times 10^6$ |
| Thiocyclam oxalate | 87.5% | 19.5 | 16.4 | 24.8 | 54.2 |
| Thiocyclam HCl | 100% | 2.22 | 0.71 | 4.15 | 1.899 |
| D +9 | | | | | |
| Cartap | 50% | 15.6 | 0.027 | 8.923.2 | 4.566.3 |
| Thiocyclam oxalate | 87.5% | 15.3 | 1.6 | 147.6 | 138.3 |
| Thiocyclam HCl | 100% | 2.23 | 0.12 | 38.9 | 4.905 |
| D +14 | | | | | |
| Cartap | 50% | 10.4 | 0.05 | 2,098.7 | 910.4 |
| Thiocyclam oxalate | 87.5% | 15.7 | 1.12 | 219 | 153.1 |
| Thiocyclam HCl | 100% | 0.82 | 0.018 | 386.3 | 7,910 |

LC stands for "Lethal Concentration". LC values refer to the concentration of a chemical required to kill a certain proportion of a population of pests. The concentration of the chemical that kills 50 percent of the pests during the observation period is the LC50 value and a concentration that kills 90 percent of a population is LC90.

LD stands for "Lethal Dose". LD50 is the amount of an ingested substance that kills 50 percent of a test sample and LC90 is the lethal dose that kills 90 percent of the test sample.

As can be seen from the results in the examples, thiocyclam hydrochloride with high purity has been manufactured using the methods described herein, so that a low concentration of thiocyclam hydrochloride can be used to effectively eliminate insects similar to or better than prior known insecticides.

In example 1, approximately 4 times less thiocyclam hydrochloride was ingested by the moths at LC50 compared to cartap and approximately 9 times less at LC90 compared to cartap. The thiocyclam hydrochloride produced by the methods provided herein also achieved an LC50 and LC90 at significantly lower concentrations than thiocyclam oxalate. In example 2, the LC50 of the soybean looper was achieved with approximately 6 times less thiocyclam hydrochloride than cartap and approximately 20 times less thiocyclam hydrochloride than thiocyclam oxalate. The LC90 of the soybean looper was orders of magnitude smaller using thiocyclam hydrochloride compared to thiocyclam oxalate, and the LC90 for thiocyclam hydrochloride was more than three times lower than the concentration of cartap. In example 3, all three insecticides performed similarly to eliminate the aphids on radish plants. In example 4, the thiocyclam hydrochloride outperforms the other insecticides significantly for achieving LD50, on all assessment days. At all assessment days, the LD90 was achieved at the lowest concentration using thiocyclam oxalate. On days 7 and 9, thiocyclam hydrochloride achieved the LD90 at a lower application concentration compared to cartap.

The use of the thiocyclam hydrochloride composition embodiments is in no way restricted to these genera, but also extends in the same manner to other insects and other crops. The novel high purity manufacturing method for thiocyclam hydrochloride has surprisingly allowed for improved insecticidal qualities when the thiocyclam hydrochloride is used in insecticidal compositions and applied to agricultural crops.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention.

In addition, it shall be pointed out that specific technical features described in the above specific embodiments, if reconcilable, can be combined in any appropriate manner, and in order to avoid unnecessary repetition, various possible combination manners are not otherwise stated herein anymore.

The invention claimed is:

1. A method of manufacturing N,N-dimethyl-1,2,3-trithian-5-ylamine hydrochloride, comprising adding an aqueous saline solution to a provided mixture of thiosulfuric acid S,S'-[2-(dimethylamino)trimethylene] ester monosodium salt and sodium hydroxide, and adding an acid to the mixture to provide solid N,N-dimethyl-1,2,3-trithian-5-ylamine hydrochloride with a purity greater than 95%.

2. The method according to claim 1, wherein the solid N,N-dimethyl-1,2,3-trithian-5-ylamine hydrochloride obtained is washed with an organic solvent selected from methyl-t-butyl ether, toluene, isopropanol, and mixtures thereof.

3. The method according to claim 1, wherein the aqueous saline solution comprises sodium chloride.

4. The method according to claim 1, wherein the temperature during the step of addition of the aqueous saline solution to the mixture of thiosulfuric acid S,S'-[2-(dimethylamino)trimethylene] ester monosodium salt and sodium hydroxide is between −10 to −25° C.

5. The method according to claim 4, wherein the temperature during the step of addition of the aqueous saline solution to the mixture of thiosulfuric acid S,S'-[2-(dimethylamino)trimethylene]ester monosodium salt and sodium hydroxide is between −15 to −18° C.

6. The method according to claim 1, wherein the acid is 2M ethereal hydrochloric acid.

7. The method according to claim 6, further comprising adding 2M hydrochloric acid in isopropanol to the mixture to obtain solid reaction product.

8. The method according to claim 1, wherein the aqueous saline solution comprises sodium sulfide.

9. The method according to claim 1, wherein the % yield of N,N-dimethyl-1,2,3-trithian-5-ylamine hydrochloride is greater than 30%.

10. The method according to claim 1, wherein the % yield of N,N-dimethyl-1,2,3-trithian-5-ylamine hydrochloride is greater than 60%.

* * * * *